United States Patent [19]

Salzman et al.

[11] 4,200,802

[45] Apr. 29, 1980

[54] PARABOLIC CELL ANALYZER

[75] Inventors: Gary C. Salzman; Mary J. Skogen Hagenson, both of Los Alamos, N. Mex.

[73] Assignee: The United States of America as represented by the United States Department of Energy, Washington, D.C.

[21] Appl. No.: 24,762

[22] Filed: Mar. 28, 1979

[51] Int. Cl.$^2$ ............................................. G01N 21/38
[52] U.S. Cl. ............................ 250/461 B; 250/358 R; 356/318
[58] Field of Search ............... 250/461 B, 461 R, 458, 250/372, 343, 345, 495; 356/317, 318

[56] References Cited

U.S. PATENT DOCUMENTS

| 3,946,239 | 3/1976 | Salzman et al. | 250/461 B |
| 4,013,892 | 3/1977 | Udart | 250/495 |

Primary Examiner—Davis L. Willis
Attorney, Agent, or Firm—R. V. Lupo; Paul D. Gaetjens; Robert W. Weig

[57] ABSTRACT

The disclosure is directed to a cell analysis apparatus incorporating a paraboloidal cavity for maximum utilization for improved cell characteristic monitoring.

10 Claims, 3 Drawing Figures

PARABOLIC CELL ANALYZER

FIELD OF THE INVENTION

The invention relates to cellular flow systems and more particularly to a cellular flow system utilizing paraboloidal reflective chambers.

BACKGROUND OF THE INVENTION

Flow microfluorometers which are valuable in many areas of biological research typically use a laser as an excitation source and collect about 2.5% of the total cell fluorescence using standard optics. There is an existing need for advanced instrumentation so that more demanding biological studies can be undertaken. Among these are the detection of life from bioluminescent reactions, quantitative human karyotyping, and determining the DNA content of peripheral lymphocytes for genetic analysis. Such advanced instruments will provide increased resolution, increased light collecting efficiency, and increased system versatility and applicability utilizing broad band emitting, i.e., 250-1000 nanometer (nm) light sources.

One advanced instrument is that described in U.S. Pat. No. 3,946,239 to Salzman et al. This patent is directed to a cell flow system utilizing an ellipsoidal flow chamber having light reflective walls and providing greatly increased signal-to-noise ratios over those obtained by prior art systems. The ellipsoidal cell flow system provides enhanced resolution particularly valuable for viewing weakly fluorescent particles such as bacteria and asymmetric particles such as chromosomes and mammalian cells.

SUMMARY OF THE INVENTION

In accordance with the present invention there is provided a cell analysis apparatus comprising a housing containing a paraboloidal cavity having an axis of rotation, a focus and light reflecting walls. Cells and a beam of essentially parallel light rays pass through the focus so as to meet perpendicularly thereat. Light scattered or fluoresced by the cells passing through the beam is collected after it reflects from the walls of the cavity. Intensity distribution of the light is utilized to determine preselected characteristics of the cells. Reflected fluoresced or original scattered light can be collected to provide a total scatter signal. In the case of reflected light, a scatter spectrum, and in the case of fluorescent light, a spectrum of fluorescence, can be obtained.

One object of the present invention is to minimize fluid flow path and increase flow stability while increasing overall collection efficiency in a cell flow system.

Another object of the present invention is to provide high resolution cell sizing.

Yet another object of the instant invention is to provide asymmetric cell orientation information.

An advantage of the instant invention is that collection efficiency is on the order of about 80%.

Another advantage of the instant invention is that total scatter signal can be collected.

BRIEF DESCRIPTION OF THE DRAWINGS

Other objects and advantages of the instant invention will be apparent to those skilled in the art from the following description with reference to the appended drawings wherein like numbers denote like parts and wherein.

DETAILED DESCRIPTION OF THE PREFERRED EMBODIMENT OF THE INVENTION

Figure 1:
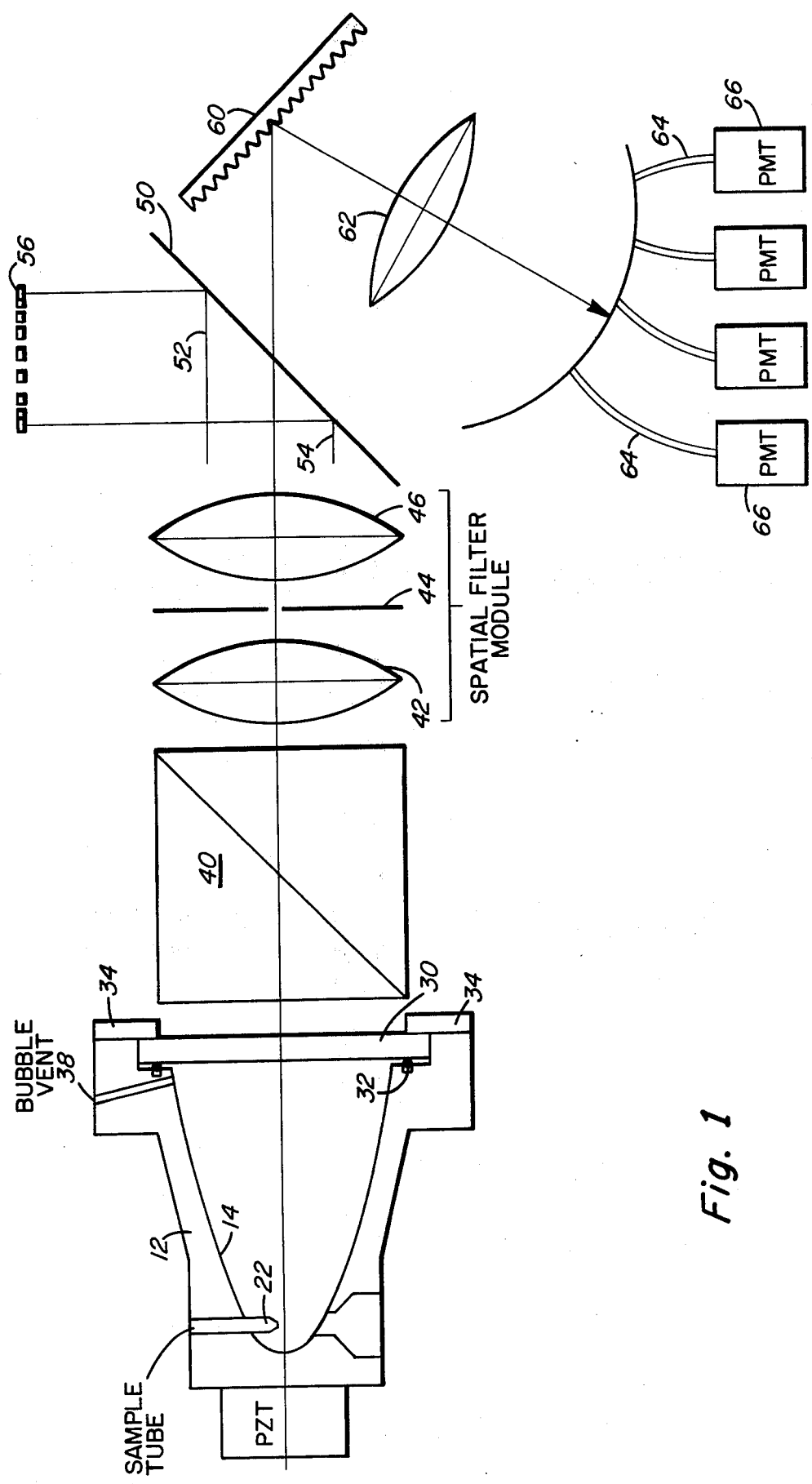
FIG. 1 illustrates a system in accordance with the present invention.
Figure 3:
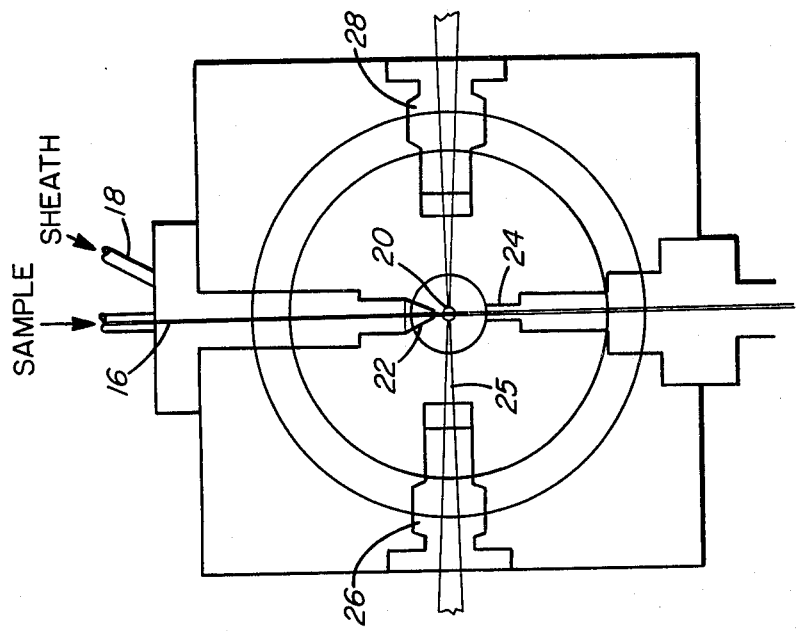
FIG. 3 depicts another cross sectional view of the cavity containing housing.
Figure 2:
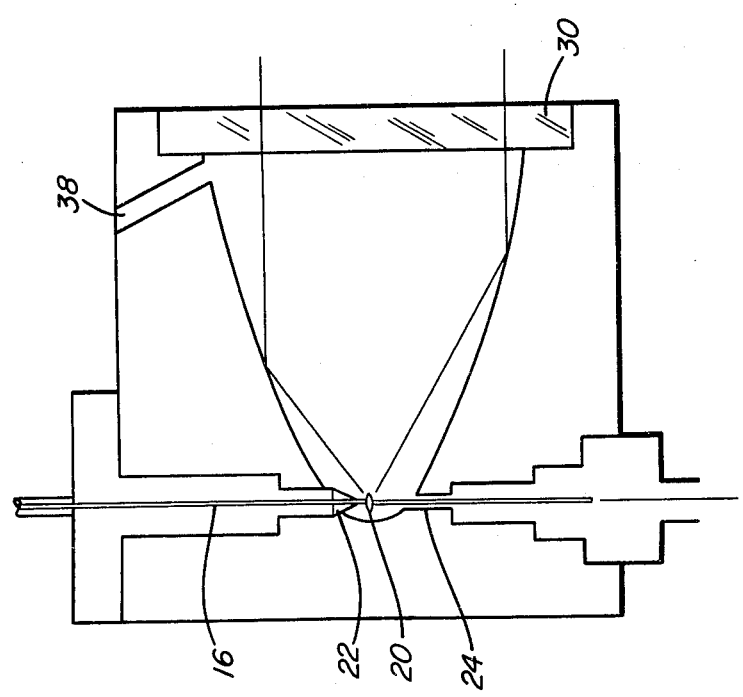
FIG. 2 shows a cross sectional view of the cavity containing housing.

Reference is now made to FIG. 1 which shows a housing 12 containing a paraboloidal cavity having a continuous wall or walls 14. In the preferred embodiment the paraboloid of revolution may have, for example, a 2.0 millimeter (mm) focal length, a depth of 40 mm, and an aperture of 35.77 mm. The walls 14 are coated with a thin evaporated layer of gold to provide reflectance within the desired spectrum, i.e., between about 250 and 1000 nm. Apertures in the surface have been made as small as possible to preserve maximum collection efficiency. As better seen in FIG. 3, a sample tube 16 and a sheath tube 18 provide pathways for the sample containing fluid and the sheath fluid to be introduced into the cavity and to pass through the focus 20 of the paraboloid of revolution. The fluids enter through a nozzle 22 and after passing through the focus, are received by a collecting tube 24. It is important to note that nozzle 22 projects into the chamber to provide a minimal transit distance for the sample and sheath fluids prior to their passage through the focus 20. The chamber is fluid filled, usually with distilled water. A laser beam 25 is directed through the focus 20, entering through a beam injector 26 and exiting through a beam receiving member 28. In the preferred embodiment an argon ion laser is utilized.

In the preferred embodiment having the dimensions previously desired, inlet nozzle 22 extends 3 mm into the paraboloid thereby injecting the sample and sheath fluid 1 mm above focal point 20. Nozzle 22 is coupled to a pressure system of a type well known to those versed in the art, which provides independent control of the sample and sheath fluids, resulting in very fine sample stream control. In practice, a laminar sample stream as narrow as 6.0 micrometers ($\mu$m) in diameter can be maintained for over an hour.

The light emitted from the paraboloid is primarily a collimated beam of fluorescence and scattered light about 35 mm in diameter which passes through a quartz window 30 sealed to the chamber by means of an O-ring 32 and clamping member 34. The chamber is filled with fluid through nozzle 22 while vacuum is applied to a bubble vent 38.

A removeable beam splitter 40 can be provided for viewing the interior of the chamber. A plano-convex lens 42 is utilized to focus the light output onto a 500 $\mu$m aperture in an opaque screen 44. Light passing through the aperture in screen 44 is collimated by a biconvex lens 46 also focused on the aperture in screen 44. This combination of lenses and the aperture provides a spatial filter for filtering out fluorescence and scattered light which is not initially collimated. Light which is not initially collimated is that light which has not been reflected by the surface of the paraboloid. The spatial filter produces a collimated beam which is about 16 mm in diameter in the preferred embodiment. A fluorescent beam of this size, once transmitted through a 488 nm interference filter, will illuminate about 90% of the face of an RCA 4526 photomultiplier tube.

Light passing through the spatial filter is directed onto a dichroic beam splitter 50. Light which is at a 90° scatter would lie in beam path 52 and that which is at a −90° scatter, in beam path 54. Thus, the scattered light is distributed across a photodetector ring 56 which, in the preferred embodiment, has 60 detectors located about every 5.6° around the circumference of the ring. Light which passes through dichroic beam splitter 50 is directed onto a low resolution diffraction grating 60, such as one having about 300 lines/mm. Diffraction grating 60 diffracts light into several diffraction orders as is well known. A lens 62 directs the first order of diffraction of fluoresced light onto the ends of fiber optic light guides 64, so that a sample of the fluorescent spectrum can be collected by, for example, photomultiplier tubes 66. Therefore, a sample of the fluorescent spectrum at a number of wavelength intervals can be collected as well as a sample of the scattered light at a variety of angles from stained cells on a cell-by-cell basis. A plurality of fluorescence spectra provides a variety of information including, but not limited to, enhanced signal to noise ratios in spectral regions of interest, since undesired wavelengths are excluded, and increased spectral resolution compared to two color fluorescence, providing for greater in-depth studies of particles stained with one or more photochromes.

The high efficiency of the system of the invention provides for the analysis of weakly fluorescent particles which could not be detected above noise levels in typical prior art cell analysis systems because the paraboloidal cavity improves resolution in cases where particle fluorescence is not bright and reduces artifacts seen by systems with small angle illumination and collection optics. The high efficiency of the paraboloid structure also permits the use of a less powerful laser than required in typical prior systems.

The paraboloidal surface may be utilized for illumination as well as collection. The advantage of this is uniform excitation of particles at the focal point. Since no biological article is perfectly symmetric, artifacts can be introduced with the fluorescent signals when only focused beam illumination is utilized.

The various features and advantages of the invention are thought to be clear from the foregoing description. However, various other features and advantages not specifically enumerated will undoubtedly occur to those versed in the art, as likewise will many variations and modifications of the preferred embodiment illustrated, all of which may be achieved without departing from the spirit and scope of the invention as defined by the following claims.

What we claim is:

1. A cell analysis apparatus comprising:
   a housing containing a paraboloidal cavity having an axis of rotation, a focus, and light reflecting walls;
   means for passing cells to be analyzed through said focus of said paraboloidal cavity;
   means for directing a beam of essentially parallel light rays through said focus so as to impinge upon any cells passing therethrough; and
   means for selectively collecting light reflected by cells passing through said beam at said focus to determine therefrom preselected characteristics of said cells.

2. The invention of claim 1 wherein substantially all said reflected light is collected to provide a total scatter signal.

3. The invention of claim 1 wherein said selective light collecting means comprises means for collecting only light reflected from said cavity walls which exits said cavity parallel to its axis of rotation.

4. The invention of claim 3 wherein said collecting means comprises a spatial filter.

5. The invention of claim 3 wherein said collecting means comprises a photodetector ring array.

6. The invention of claim 5 wherein said array comprises about sixty detectors dispersed about every 5.6 degrees.

7. A cell analysis apparatus comprising:
   a housing containing a paraboloidal cavity having an axis of rotation, a focus, and light reflecting walls;
   means for passing cells to be analyzed substantially through said focus of said paraboloidal cavity;
   means for directing a beam of essentially parallel light of a selected wavelength through said focus to impinge upon any cell passing therethrough and to cause said cell to fluoresce; and
   means for selectively collecting light fluoresced by said cells passing through said beam at said focus to determine therefrom certain cellular characteristics.

8. The invention of claim 7 wherein said collecting means comprises a spatial filter for passing only fluoresced light travelling parallel to said axis of rotation, a diffraction grating for receiving said parallel fluoresced light and for diffracting said light in at least a first order diffraction spectrum, means for focusing said first order diffraction spectrum onto a focal plane, and means for quantitatively detecting the diffraction spectrum incident on said focal plane.

9. The invention of claim 8 wherein said quantitative detecting means comprises a plurality of photomultiplier tubes.

10. A chamber structure for use in a cell analysis system comprising:
    a housing containing a paraboloidal cavity having a focus and an axis of rotation;
    means for passing a laser beam through said focus and essentially perpendicular to said axis of rotation; and
    means comprising a nozzle protruding into said chamber structure essentially perpendicular to said axis of rotation and said laser beam for passing a stream of cells to be analyzed through said beam essentially at said focus.

* * * * *